United States Patent
Hansen

(10) Patent No.: US 10,016,201 B2
(45) Date of Patent: Jul. 10, 2018

(54) VASCULAR PLUG

(71) Applicant: COOK MEDICAL TECHNOLOGIES LLC, Bloomington, IN (US)

(72) Inventor: Christina Rauff Hansen, Valby (DK)

(73) Assignee: Cook Medical Technologies LLC, Bloomington, IN (US)

( * ) Notice: Subject to any disclaimer, the term of this patent is extended or adjusted under 35 U.S.C. 154(b) by 294 days.

(21) Appl. No.: 14/268,397

(22) Filed: May 2, 2014

(65) Prior Publication Data

US 2014/0330303 A1    Nov. 6, 2014

(30) Foreign Application Priority Data

May 2, 2013  (GB) .................................. 1307965.2
Sep. 11, 2013 (GB) .................................. 1316157.5

(51) Int. Cl.
  *A61B 17/08*  (2006.01)
  *A61B 17/12*  (2006.01)
  *A61F 2/01*  (2006.01)

(52) U.S. Cl.
  CPC .. *A61B 17/12109* (2013.01); *A61B 17/12031* (2013.01); *A61B 17/12172* (2013.01);
  (Continued)

(58) Field of Classification Search
  CPC ........ A61B 17/12109; A61B 17/12177; A61B 2017/1205; A61B 17/12031;
  (Continued)

(56) References Cited

U.S. PATENT DOCUMENTS 6,450,165 B1 * 9/2002 Silver .................... A62B 17/04
                                            128/201.22
6,656,351 B2 * 12/2003 Boyle .................... A61F 2/013
                                            210/136
(Continued)

FOREIGN PATENT DOCUMENTS

CN       101390387 A     3/2009
EP        0664107         1/1995
(Continued)

OTHER PUBLICATIONS

British Office Action dated Nov. 3, 2014 for GB 1316157.5 in corresponding application.
(Continued)

*Primary Examiner* — Jing Ou
*Assistant Examiner* — Jing Rui Ou
(74) *Attorney, Agent, or Firm* — Brinks Gilson & Lione

(57) ABSTRACT

A vascular plug has a frame or skeleton which includes a ring of spring material and, attached to the frame, a cover of impervious or porous material. The plug is able to open a cup configuration when in a deployed condition, so as to provide an occlusion barrier to blood flow. The frame can be radially contracted by twisting into a multi-coiled configuration for deployment through an introducer. The vascular plug has a very short deployment length, making it suitable for deployment in precise locations and is also able to expand to a variety of operating diameters, thereby being suitable for a range of vessel sizes.

15 Claims, 4 Drawing Sheets

(52) U.S. Cl.
CPC .......... *A61B 17/12177* (2013.01); *A61F 2/01*
(2013.01); *A61B 2017/1205* (2013.01); *A61F*
*2002/011* (2013.01); *A61F 2002/016*
(2013.01); *A61F 2230/001* (2013.01); *A61F*
*2230/0008* (2013.01); *A61F 2230/0091*
(2013.01); *A61F 2230/0095* (2013.01)

(58) Field of Classification Search
CPC ................ A61B 17/12172; A61F 2/01; A61F
2002/011; A61F 2230/001; A61F
2230/0095; A61F 2002/016; A61F
2230/0008; A61F 2230/0091
See application file for complete search history.

(56) References Cited

U.S. PATENT DOCUMENTS

| | | | |
|---|---|---|---|
| 8,226,679 B2* | 7/2012 | Johnson | A61F 2/01 210/435 |
| 2001/0039450 A1 | 11/2001 | Pavcnik et al. | |
| 2003/0187475 A1* | 10/2003 | Tsugita | A61F 2/01 606/200 |
| 2004/0049262 A1* | 3/2004 | Obermiller | A61F 2/2418 623/1.15 |
| 2006/0020285 A1* | 1/2006 | Niermann | A61F 2/01 606/200 |
| 2007/0088387 A1* | 4/2007 | Eskridge | A61B 17/12022 606/213 |
| 2007/0198059 A1* | 8/2007 | Patel | A61B 17/0057 606/213 |
| 2009/0275978 A1 | 11/2009 | Yassinzadeh | |
| 2010/0179583 A1 | 7/2010 | Carpenter et al. | |
| 2010/0262219 A1* | 10/2010 | Frimerman | A61F 2/013 623/1.11 |
| 2011/0230956 A1* | 9/2011 | White | A61F 2/2412 623/1.16 |
| 2012/0046687 A1 | 2/2012 | Trommeter et al. | |
| 2012/0101572 A1* | 4/2012 | Kovalsky | A61F 2/2418 623/2.19 |

FOREIGN PATENT DOCUMENTS

| | | |
|---|---|---|
| EP | 1430839 A1 | 6/2004 |
| WO | WO 01/17435 | 3/2001 |
| WO | WO 2012/051489 A2 | 4/2012 |

OTHER PUBLICATIONS

Combined Search and Examination Report for Great Britain Patent Application No. 1316157.5 dated Mar. 12, 2014, 6 pages.
Examination Report for Great Britain Patent Application No. 1316157.5 dated May 13, 2015, 2 pages.

\* cited by examiner

VASCULAR PLUG

CROSS REFERENCE TO RELATED APPLICATIONS

This application is related to and claims the benefit of priority to British patent application number GB 1307965.2, filed May 2, 2013, and British patent application number GB 1316157.5, filed Sep. 11, 2013, which are incorporated herein by reference in their entireties.

TECHNICAL FIELD

The present invention relates to a vascular plug and to an introducer assembly including a vascular plug.

BACKGROUND ART

Vascular plugs, or occluders, are well known for occluding bodily vessels and are produced in a variety of forms. They may act to create substantially instantaneous occlusion of a vessel, in which case the structure of the plug provides an impermeable barrier to fluid, or they may act to occlude the vessel over time, in which case the plug will generally have a pervious membrane designed to slow the flow of blood through the vessel. The membrane promotes thrombosis of the blood and eventual occlusion of the vessel by the formed thrombus.

Vascular plugs are typically deployed endoluminally through the patient's vasculature up to the intended site of treatment. For this purpose, it is important to be able to compress the vascular plug radially so as to fit within an introducer assembly of a diameter which can pass readily through the patient's vasculature. To this end, it is known to have vascular occluders which are able to be pulled to an elongate form, which minimizes their lateral dimension and thus enables them to be deployed through catheters of very small diameter. While such designs of plug can optimize the delivery of the plug through the patient's vasculature, particularly where this is tortuous and/or narrow, a plug which expands from an elongate form to a shorter form cannot be positioned precisely in a patient's vessel, which can make such designs unsuitable when the treatment site is short, for example between closely located branch vessels and so on.

Vascular plugs also generally have specific operating diameters, designed to ensure occlusion as well as reliable fixation to the vessel wall so as to minimise the risk of migration of the plug over time. These plugs, however, are vessel-size specific and it is therefore necessary to determine vessel size accurately before treatment, as well as to have available for use a stock of different size plugs. Even with selection of a plug of the correct size, changes in the dimensions or shape of a vessel over time can cause imprecise occlusion and risk of migration of the plug.

Known designs of vascular plug can be found, for example, in US-2012/0,046,687, US-2010/0,179,583, US-2009/0,275,978, WO-01/17,435 and EP-0,664,107.

SUMMARY OF THE INVENTION

The present invention seeks to provide an improved vascular plug and an introducer assembly for such a vascular plug.

According to a first aspect of the present invention, there is provided a vascular plug including at least one resilient frame element, a cover attached to the at least one resilient frame, the frame element having a first, radially expanded deployed condition and a second, multi-coil configuration in which the coils lie adjacent and substantially coaxial with one another, the same element being compressible by twisting from the first to the second configuration, wherein when in the second configuration, the plug is not substantially lengthened from the first condition.

This structure of vascular plug is such that in the compressed form it has a short footprint and thus can be positioned in a narrow section of vessel and with precision. Furthermore, as explained below, the plug is able to expand to a variety of diameters, thus making it suitable for deployment in a range of vessel sizes. Moreover, the structure provides for continuous generation of an expansion force, which can assist in holding the plug properly against the vessel wall, thus optimizing occlusion and minimizing the risk of migration.

Preferably, the at least one resilient frame element is in the form of a ring to which the cover is fitted. A ring shape provides a strong support frame to the plug and is also readily twistable for folding.

Advantageously, the first frame element is constrained into a curved shape. Such a shape can be optimal for deployment in a patient's vessel and to provide good patency to the vessel wall.

In an embodiment, the first frame element is constrained into the curved shape by the cover or a tether.

There is preferably provided a second frame element coupled to the resilient frame element. Advantageously, the second frame element includes a frame ring constrained to an oval shape by a cover or tether. The plug preferably includes a second cover extending between the resilient frame element and the second frame element. The second cover in practice acts as the barrier to flow when the plug is deployed in a vessel, this barrier being a barrier to blood in the case of a plug configured as an occluder and being a filter for trapping debris in the case of a plug configured as a filter.

In a practical embodiment, the second frame element and/or the second cover cause the resilient frame element to curve in a direction orthogonal to the (or a) curvature of the first occluding barrier.

Preferably, there is provided a third cover extending across the second frame element.

Advantageously, the second frame element is deformable to the resilient frame element so as substantially to align with the resilient frame element.

In the preferred embodiment, in the radially expanded deployed condition the resilient frame element provides an outer perimeter of the plug, which outer perimeter in use abuts against a vessel wall and the or a second cover extends across the outer perimeter.

The each frame element is preferably in the form of at least one ring.

The each frame element may be formed of a spring material. The each frame element is formed from a shape memory material.

The cover or covers may be made of an impervious material, a substantially impervious material, a porous material, a mesh or any combination thereof.

In one embodiment, at least one cover is formed of ultra-high-molecular-weight polyethylene.

Preferably, the resilient frame element is compressible by twisting to a diameter 5 to 10 times smaller than its diameter in its radially expanded deployed condition.

According to another aspect of the present invention, there is provided an introducer assembly including a delivery catheter; and a vascular plug according to the first aspect of the invention, disposed in the delivery catheter; wherein the vascular plug is disposed in the delivery catheter in the multi-coil configuration.

The introducer assembly preferably includes a pusher element disposed in the delivery catheter, the pusher element including a distal end adjacent the vascular plug.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

The preferred embodiments disclosed herein relate to a vascular plug which is intended to be used for embolization, that is as a device deployed in a patient's vessel to occlude the vessel, arrest or prevent hemorrhaging or devitalizing a structure or organ by occluding its blood supply. The device can be used, for example, to stop blood flow to tumors, into aneurysms, to stop blood flow to organs prior to their removal and to stop abnormal blood flow such as arteriovenous malformation (AVM) or arteriovenous fistula (AVF), for stopping bleeding and so on.

The device may provide instantaneous occlusion of a vessel, for which purpose the vascular plug is designed so as to be substantially impervious and to stop all of or practically all of the flow of blood past the plug substantially immediately on deployment of the plug. In other embodiments, the plug may be porous and designed so as to slow the flow of blood through the plug, promoting embolization and resultant occlusion of the vessel after formation of thrombi.

The vascular plug disclosed herein can also be structured to operate as a vascular filter, in which case the frame elements of the plug are covered in a porous material such as a mesh able to trap debris within a patient's blood but to allow the passage of blood through the plug. The skilled person will appreciate that the difference in the function of the plug, that is as an occluder or as a filter, will be dependent upon the cover material used and that all other elements and characteristics of the structure can be the same for both types of plug.

As is described in detail below, the embodiments of vascular plug taught herein are able to be twisted into what could be described as a folded coil configuration and having a diameter substantially less than the diameter of the plug when unfolded and practically five to ten times smaller than its unfolded diameter. As a result of this, it is possible to fold the plug to a very small delivery diameter and also in such a manner, as will become apparent below, that the plug when in the folded condition is not substantially lengthened and in practice is significantly shorter than known vascular plug structures in their delivery configurations. In most embodiments, the folded plug will have a length which is shorter than its length when deployed.

The cup shape may have a range of effective deployment diameters able to block or filter fluid flow through the plug over a range of vessel sizes. As a result, a single sized vascular plug is suitable for different vessels and different patients.

Figure 1:
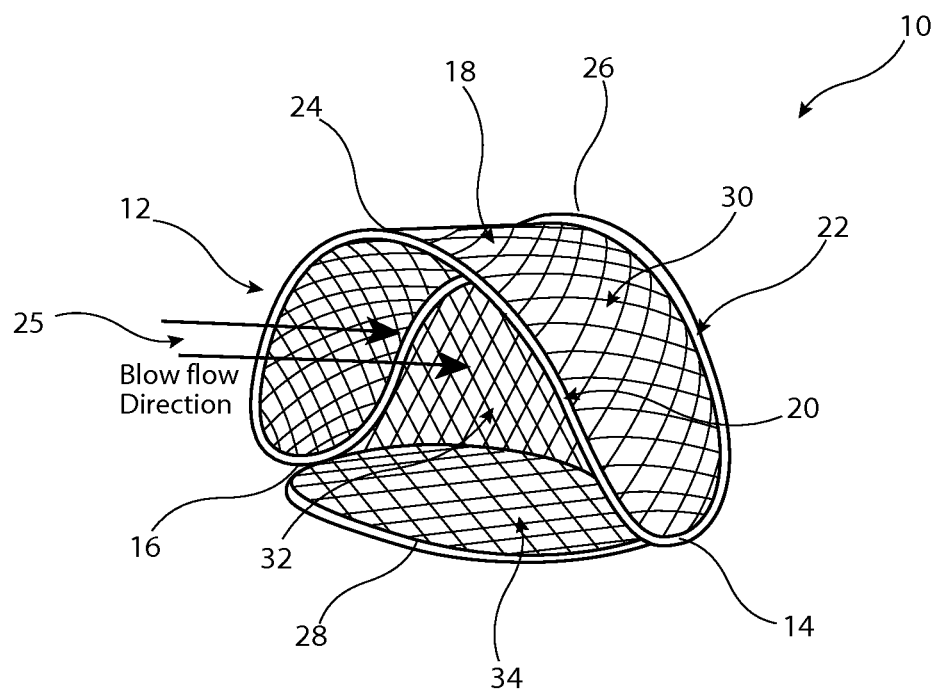
FIG. 1 is a side elevational view of an embodiment of vascular plug in an open or deployed configuration.

Referring first to FIG. 1, there is shown a preferred embodiment of vascular plug 10, which in the Figure is in its operative or deployed condition.

The plug 10 includes a first frame or skeleton 12, which in this embodiment could be described as a ring, preferably made of a metallic or polymeric material which has spring characteristics. In a preferred embodiment, the first frame 12 is made of a shape memory material, for instance a metal alloy or polymer. Nitinol is a particularly suitable material. Other embodiments may be made of a spring material such as spring steel, for example.

The first frame or skeleton 12 may be made of a single wire in an endless loop, hereinafter referred to as a ring, but may equally be made of a plurality of wires or threads which may or may not be coupled together, for example by intertwining.

The first frame 12, in the deployed configuration, is curved into a U-shape so as to have two base points 14, 16 and a summit 18. Between the base points 14, 16 and the summit 18, the first frame 12 extends along curved edges 20, 22 to respective summit points 24, 26.

Attached to the first frame 12 is a second frame element 28, in particular at the base points 14, 16. The second frame element 28 is preferably of oval shape and may be formed of the same material and in the same manner as the first frame element.

The first frame element 12 has a cover 30 which extends across it, in a curved configuration when the plug 10 is deployed as shown in FIG. 1. The cover 30 is preferably a woven or knitted textile material, although in other embodiments may be made of a sheet material. Preferred material for the cover 30 is an ultra-high molecular weight polyethylene such as Dyneema™, most preferably of 10 DTEX specification. Such material is useful in the fabrication of a plug acting as an occluder. Other embodiments may use a cover 30 of porous nature, such as a porous mesh, thereby to form a filter. The cover 30 may be of synthetic material or natural materials such as SIS.

The cover 30 may have an oval shape, which in the preferred embodiment trains the first frame element 12 to an oval shape prior to curving in the orthogonal direction shown in FIG. 1. Another embodiment provides a tether (not shown) to constrain the first frame element 12 to an oval.

The plug 10 includes a second cover 32 which extends from the curved edge 22 to the adjacent edge of the second frame element 28, thereby to form what could be described as an upstanding cover across the gap between the frame elements 12 and 28. In practice, as will be apparent from FIG. 1, the second cover 34 will be at the distal or downstream end of the plug 10, such that blood will flow into the internal space or chamber of the plug.

A third cover 34 extends across the second frame element 28, thereby to close this off.

The first frame element 12 is constrained to the curved shape shown by the second frame element 28, but could in other embodiments be constrained by a tether or even by the second cover 32. Similarly, as explained above, the side elements 22, 24 could be constrained towards one another by a suitable width to the first cover 30 and/or by a suitable tether. Similarly, the second frame element 28 could be constrained into an annular shape by having the second cover 32 of an oval shape and/or by a suitable tether.

In the deployed configuration shown in FIG. 1, the plug would reside in a patient's vessel such that the first frame sides 22 and 24 and the second frame element 28 abut the vessel wall, with the second cover 32 thus extending across the vessel. It will be appreciated that the plug 10 could also extend across the vessel wall in this manner even when not fully opened, for instance when deployed in a smaller vessel, in which case the first frame element 12 may be curved to a smaller diameter and the second frame element 28 suitably compressed.

In FIG. 1, the arrow 25 shows the intended direction of blood flow into the device 10. This is achieved by deploying the device 10 in the vessel such that the cover 32 is downstream, thereby to have the chamber formed by the covers 30-34 open to the blood flow.

It will be appreciated that the covers 30, 32 and 34 may all be formed of the same material. It is not excluded, though, that they may be made of different materials. For instance, the first and third covers 30, 34 could be made of an impervious material whereas the second cover 32 could be made of a porous material, enabling the plug to act as a filter; and vice versa, enabling the plug 120 to act as an occluder.

Referring now to FIGS. 2 to 7, the vascular plug 10 of FIG. 1 is shown in various stages of being folded and twisted in preparation for fitting into an introducer assembly for deployment endoluminally in a patient.

Figure 2:
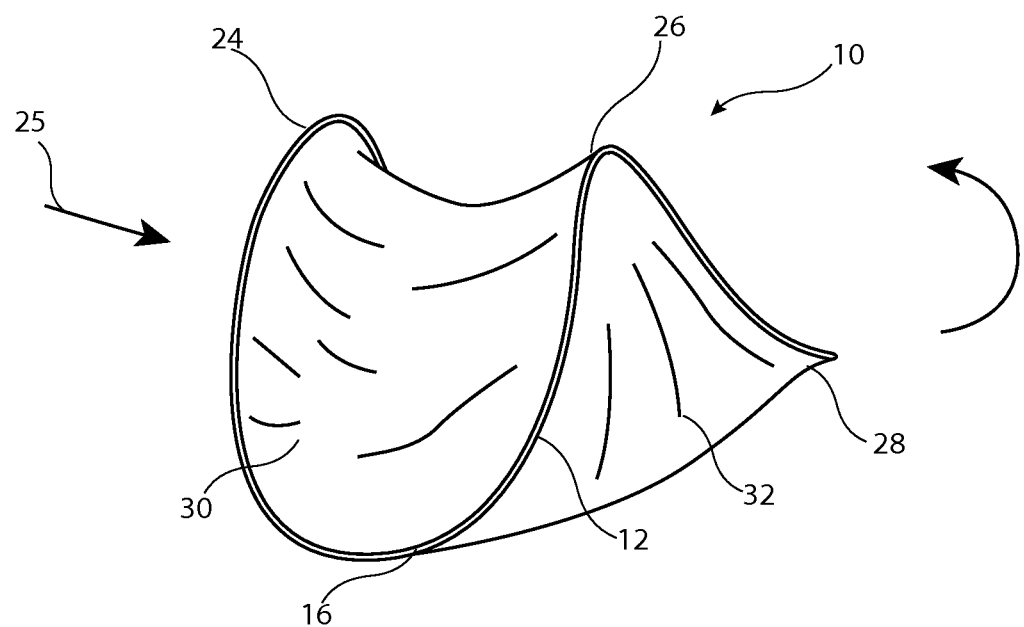
FIGS. 2 to 7 are side elevational views of the vascular plug of FIG. 1 in varying stages of radial twisting.

In FIG. 2 the second frame element 28 is brought up towards the first frame element 12 and thus such that the second cover 32 is folded on itself. As will be appreciated from FIG. 2, it is preferred that the second frame element 28 has a size and shape equivalent to the that of the part of the first frame element 12 from the points at which they are attached to one another (for example half circular), such that the second frame element 28 becomes aligned with the first frame element 12. This allows the two frame elements then to be twisted together, as will become apparent from the following Figures.

Figure 3:
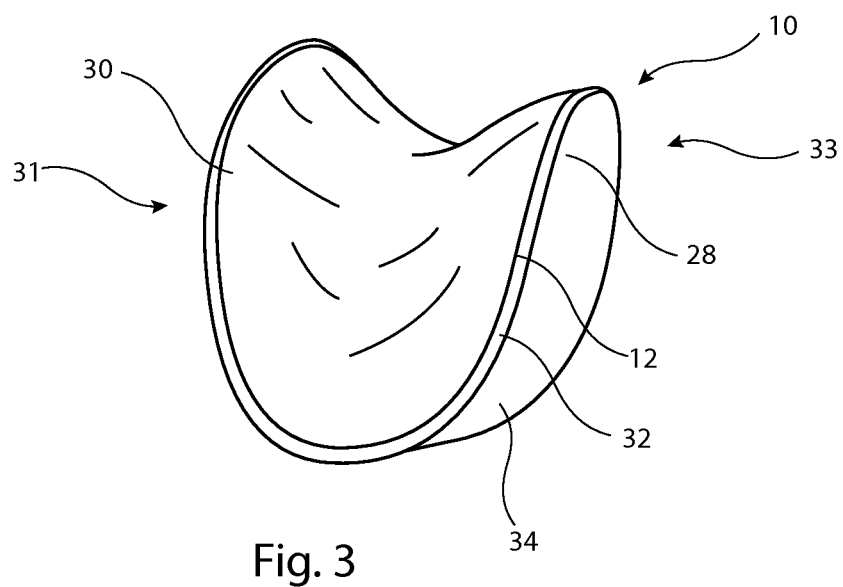
Figure 4:
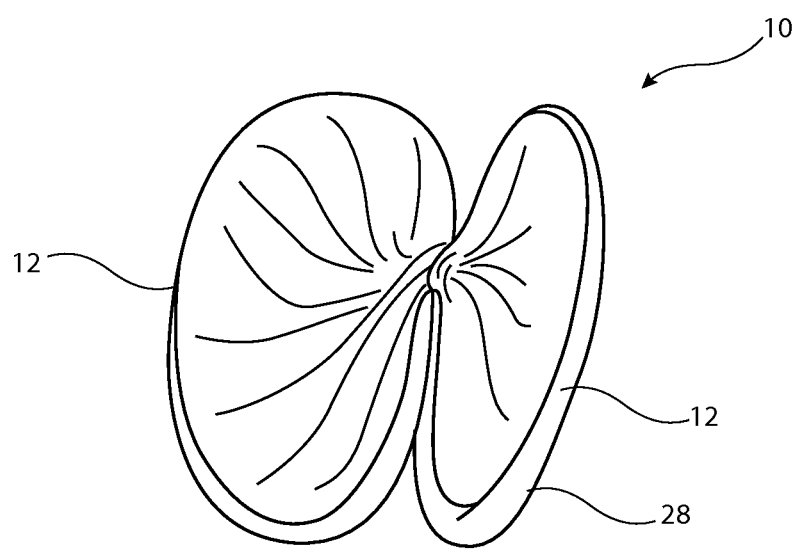
Figure 5:
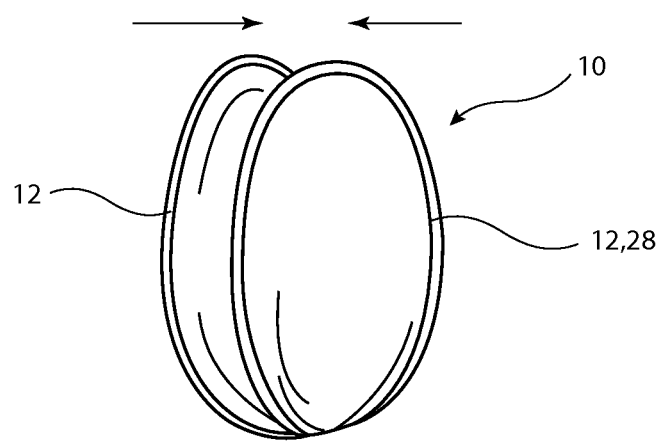
Figure 6:
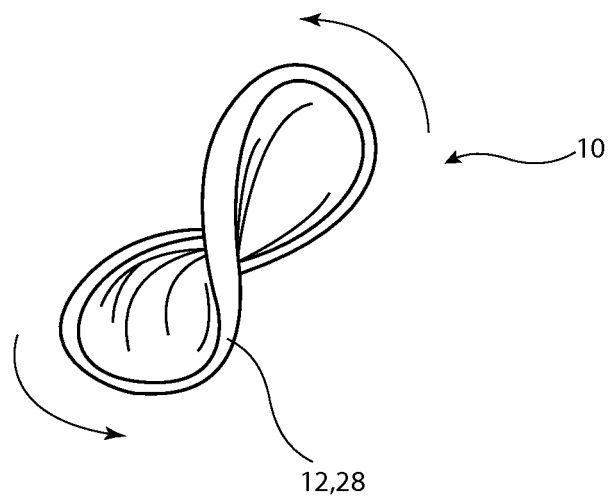
Figure 7:
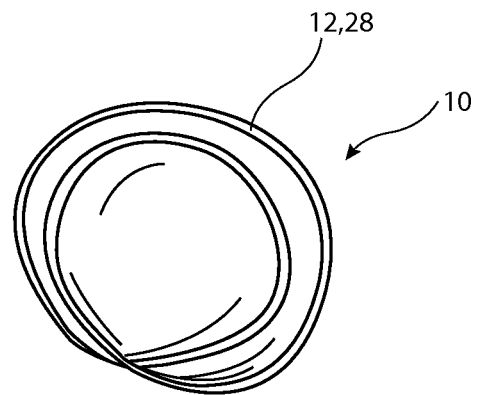

Referring to FIG. 3, once the second frame element has been brought up to the frame element 12, the two sides 31, 33 of the frame are held and rotated in opposite directions, as depicted by the arrows in the Figure. The resultant twisted configuration is depicted in FIG. 4, in which it can be seen that the frame elements 12, 28 of the plug 10, from their configuration of FIG. 3, have been twisted around themselves by rotation of opposing sides of the frame assembly 12, 28. They are shown fully twisted by at least 180 degrees in FIG. 5, thereby to form two rings of 50% of the original diameter of folded frame assembly 12, 28. FIG. 5 shows the two turns of the frame assembly 12, 28 pushed together, from which position the structure can be twisted yet again, as shown in FIG. 6. It is preferred, as will be apparent form the arrows in FIG. 6, that this second twisting action is carried out about an axis or rotation orthogonal to that of the first twist, shown in FIGS. 3 and 4. The frame rings thus produced in the second twist of FIG. 6 can be pushed together one more time to create a twisted and folded assembly as shown in FIG. 7 and having a diameter one quarter of that of FIG. 3. In the preferred embodiment, the assembly can be twisted in this manner repeatedly, such that the final diameter of the folded assembly is no more than one fifth or one tenth of the original diameter. The skilled person will appreciate that with each twisting of the resultant frame ring, the diameter will half.

The springiness of the frame assembly 12, 28 will generate a continuous opening force which will cause it to open out in the absence of any restraining force, and that thus on releasing of the structure from its configuration of, for example, FIG. 7, it will untwist and open out again, in a reverse sequence to that shown in FIGS. 1 to 7. This is how the plug 10 unravels and expands in a vessel following its placement by means of an introducer assembly, as described in further detail below.

It will be apparent that the structure of vascular plug 10 shown in FIG. 1, when configured as an occluder, is able to provide substantially instantaneous occlusion of a vessel in which it is deployed, in the case where the covers 30, 32 and 34 are impermeable to blood. As described above, the covers 30, 32 and 34 may be made of a porous material of porosity sufficient to slow the flow of blood through the plug 10 once deployed so as to promote embolization at the site of the plug 10, with the formed thrombi acting to provide complete occlusion of the vessel. The skilled person will be able readily to ascertain a suitable porosity for such an embodiment. Similarly, the covers 30-34 could be of a porous mesh such that the plug 10 acts as a filter.

The frame 12 of the plug 10 can expand to a variety of different open diameters and yet still retain its occluding shape, that is to have a closed cup of cover material 30-34 provided by the frame elements 12, 28. Thus, the plug 10 is suitable for fitting to a range of vessel diameters.

It is envisaged that the plug 10 could have a maximum deployment diameter which is several times its minimum deployment diameter. For example, in one embodiment the plug 10 may have minimal deployment diameter of 2.6 mm and a maximum deployment diameter of 16 mm, thus to be able to occlude any vessel having a diameter within that range. Such a vascular plug could be useful for occluding the internal iliac arteries prior to EVAR and PAVM embolization as well as for many other vessels. The plug could be used both for arterial and for venous indications.

Figure 8:
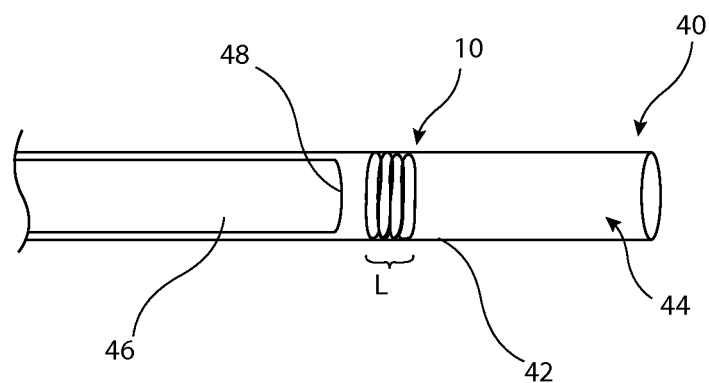
FIG. 8 is a longitudinal cross-sectional view of an introducer assembly including the vascular plug held therewithin.

Referring now to FIG. 8, there is shown the distal end 40 of an embodiment of introducer assembly for deploying the vascular plug 10 within a patient. The introducer assembly is of generally known structure and includes an elongate flexible sheath 42 which includes a distal end 44 and a proximal end (not shown) which terminates at an external manipulation unit of generally conventional form. Disposed within the sheath 42 is a pusher element 46, which also extends to the proximal end of the sheath 42. The pusher element 46 includes a pusher head 48 against which lies the vascular plug 10, which is typically in a folded configuration in the introducer assembly 40, as described below. The design of the introducer assembly 40 is such that in practice the distal end 44 thereof is fed endoluminally through the vasculature of a patient up to the location at which the vascular plug 10 is to be deployed, while the proximal end of the sheath 42 remains outside the patient. For this purpose, the introducer assembly 40 may include a guide wire, a dilator tip and other elements which are common with such assemblies and provided for facilitating the introduction of the assembly into the patient via any of the known techniques.

The vascular plug 10, by means of its structure as shown in particular in FIGS. 1 to 7, is folded on itself into what could be described as a multi-coil arrangement, achieved by twisting the frame elements 12 and 28 on themselves several times. In the preferred embodiment, the frame elements 12 and 28 can be twisted so as to have several coil turns, typically anything from around 4 to 10 or more turns.

The fact that the plug 10 can be radially constrained by such twisting or coiling action, means that in its radially constrained configuration, as shown in FIG. 8, the plug 10 has a relatively small length L, which is much shorter than the delivery lengths of prior art vascular plug configurations. As a result, the vascular plug 10 can be deployed much more precisely within the vasculature of a patient and where there is little place to locate the plug within a vessel, for example in short vessels, near closely spaced vessel side branches, and so on.

In the embodiment shown in FIG. 8, the plug 10 is deployed by driving the push element 46 forwardly towards the distal end 44 of the sheath 42 (or by pulling the sheath 42 backwardly towards the push element 46). Once the plug 10 becomes partially exposed beyond the distal end 44 of the sheath 42, it will begin to expand radially outwardly, until the frame elements 12 and 28 come into contact with the walls of the vessel. Such expansion is achieved by means of the spring force of the frame elements 12 and 28 of the plug 10, by virtue of it being compressed (by twisting) into the folded arrangement shown in the Figures. It will be appreciated that such spring force will be permanent in the case of frame elements made of spring material, but may be generated, in the case of a shape memory material, once the frame has warmed to body temperature.

Once the plug 10 has been completely withdrawn from the sheath 42, it will expand to the radially expanded deployed configuration shown in FIG. 1, constricted radially only by the amount of its oversizing relative to the vessel diameter. The partially wrapped of curved configuration of the plug 10, shown in FIG. 1, ensures that the frame elements exert a continuous radial expansion force against the vessel walls but that this force is not excessively great as to cause damage to the vessel tissue. It will be appreciated that this design of frame does not risk the problems of over-sizing which may be experienced with prior art vascular plug structures, which may cause damage or trauma to the vessel wall structure if they are significantly larger that the diameter of the vessel into which they are implanted.

Occlusion of the vessel will be virtually instantaneous in the case of a plug 10 provided with impervious cover elements 30-34, while with porous material occlusion will occur after embolization, which may take from hours to a few days.

It is to be understood that the term imperious as used herein is intended to denote an occluding propriety to the cover and thus may not be totally impervious but closed enough to prevent any significant passage of blood therethrough and thus to promote occlusion by blood stasis and subsequent thrombosis.

Although the preferred embodiments make use of a second frame element 28 of oval form, this need not have the form shown given that its function is to hold the first frame element 12 in the curved configuration. For instance, the second frame element 28 could be in the form of a tether tying the two base points 14, 16 to one another.

The invention claimed is:

1. A vascular plug including at least one resilient frame element, a first cover attached to the at least one resilient frame element, the at least one resilient frame element having a first, radially expanded deployed condition, in which the at least one resilient frame element forms a closed ring, and a second, multi-coil configuration, in which the closed ring forms at least two coils adjacent and substantially coaxial with one another the at least one resilient frame having a smaller width in the multi-coil configuration than in the radially expanded deployed condition, the at least one resilient frame element being compressible by rotating opposite sides of the frame by at least 180 degrees relative to one another from the first condition to the second configuration, wherein when in the second configuration, the plug has a length which is less than a length of the plug in the first condition, the vascular plug being detachable from a delivery assembly and implantable in a body vessel of a patient,
wherein the at least one resilient frame element is constrained into a curved shape by a second frame element coupled to the at least one resilient frame element.

2. The vascular plug according to claim 1, wherein the at least one resilient frame element is also constrained into the curved shape by the first cover.

3. The vascular plug according to claim 1, wherein the second frame element includes a frame ring constrained to an oval shape by a cover.

4. The vascular plug according to claim 1, including a second cover extending between the at least one resilient frame element and the second frame element.

5. The vascular plug according to claim 4, wherein at least one of the second frame element and the second cover causes the at least one resilient frame element to curve in a direction orthogonal to a curvature of another portion of the first cover.

6. The vascular plug according to claim 4, including a third cover extending across the second frame element.

7. The vascular plug according to claim 1, wherein the second frame element is deformable relative to the at least one resilient frame element so as substantially to align with the resilient frame element.

8. The vascular plug according to claim 1, wherein in the radially expanded deployed condition the at least one resilient frame element provides an outer perimeter of the plug, wherein the outer perimeter of the plug is configured to abut a vessel wall, and a second cover extends across the outer perimeter.

9. The vascular plug according to claim 1, wherein the at least one resilient frame element is formed of a spring material.

10. The vascular plug according to claim 1, wherein the at least one resilient frame element is formed from a shape memory material.

11. The vascular plug according to claim 1, wherein the first cover is made of an impervious material, a substantially impervious material, a porous material, a mesh or any combination thereof.

12. The vascular plug according to claim 1, wherein the cover is formed of ultra-high-molecular-weight polyethylene.

13. The vascular plug according to claim 1, wherein the at least one resilient frame element is compressible by twisting to a diameter 5 to 10 times smaller than its diameter in its radially expanded deployed condition.

14. An introducer assembly including a delivery catheter; and the vascular plug according to claim 1 disposed in the delivery catheter; wherein the vascular plug is disposed in the delivery catheter in the multi-coil configuration.

15. The introducer assembly according to claim 14, including a pusher element disposed in the delivery catheter, the pusher element including a distal end adjacent the vascular plug.

* * * * *